(12) United States Patent
Odedra et al.

(10) Patent No.: US 9,028,917 B2
(45) Date of Patent: May 12, 2015

(54) HIGH MOLECULAR WEIGHT ALKYL-ALLYL COBALTTRICARBONYL COMPLEXES AND USE THEREOF FOR PREPARING DIELECTRIC THIN FILMS

(75) Inventors: Rajesh Odedra, Victoria (CA); Neil Boag, Mytholmroyd W. Yorkshire (GB); Jeff Anthis, San Jose, CA (US); Ravi Kanjolia, North Andover, MA (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 418 days.

(21) Appl. No.: 13/388,861

(22) PCT Filed: Jul. 27, 2010

(86) PCT No.: PCT/US2010/043300
§ 371 (c)(1),
(2), (4) Date: Mar. 29, 2012

(87) PCT Pub. No.: WO2011/017068
PCT Pub. Date: Feb. 10, 2011

(65) Prior Publication Data
US 2012/0177845 A1  Jul. 12, 2012

Related U.S. Application Data

(60) Provisional application No. 61/232,219, filed on Aug. 7, 2009, provisional application No. 61/301,390, filed on Feb. 4, 2010.

(51) Int. Cl.
*C23C 16/00* (2006.01)
*C07F 15/00* (2006.01)
(Continued)

(52) U.S. Cl.
CPC .............. *C07F 15/06* (2013.01); *C23C 16/406* (2013.01); *C23C 16/45553* (2013.01)

(58) Field of Classification Search
CPC .. C07F 15/06; C23C 16/45553; C23C 16/406
USPC ................. 427/248.1, 250; 556/140
See application file for complete search history.

(56) References Cited

U.S. PATENT DOCUMENTS

| 4,388,021 A | 6/1983 | Weiss |
| 4,680,953 A | 7/1987 | Fabris |

(Continued)

FOREIGN PATENT DOCUMENTS

| JP | 2006-328526 A | 12/2006 |
| KR | 10-2008-0110897 | 12/2008 |

(Continued)

OTHER PUBLICATIONS

Dickson et al. The assesment of some cobalt and cobalt-tellurium complexes for MOCVD applications, Polyhedron, vol. 14, No. 13 pp. 2237-2245.*

(Continued)

*Primary Examiner* — Kelly M Gambetta
(74) *Attorney, Agent, or Firm* — Harness, Dickey & Pierce, P.L.C.

(57) ABSTRACT

A method for forming a cobalt-containing thin film by a vapor deposition process is provided. The method comprises using at least one precursor corresponding in structure to Formula (I); wherein $R^1$ and $R^2$ are independently $C_2$-$C_8$-alkyl; x is zero, 1 or 2; and y is zero or 1; wherein both x and y can not be zero simultaneously.

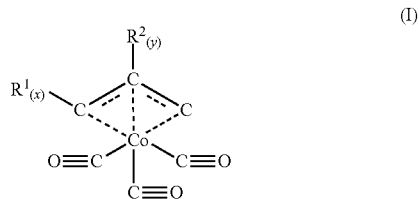

20 Claims, 6 Drawing Sheets

(51) Int. Cl.
  *C07F 15/06* (2006.01)
  *C23C 16/40* (2006.01)
  *C23C 16/455* (2006.01)

(56) References Cited

U.S. PATENT DOCUMENTS

| | | | |
|---|---|---|---|
| 4,988,159 A | 1/1991 | Turner et al. | |
| 6,541,067 B1* | 4/2003 | Marsh et al. | 427/252 |
| 6,698,728 B1 | 3/2004 | Ravetz et al. | 261/121.1 |
| 7,282,119 B2 | 10/2007 | Odedra et al. | 203/29 |
| 7,419,698 B2 | 9/2008 | Jones | 427/248.1 |
| 8,039,062 B2 | 10/2011 | Heys et al. | 427/585 |
| 2003/0096468 A1* | 5/2003 | Soininen et al. | 438/200 |
| 2007/0190684 A1 | 8/2007 | Jones | 427/255.32 |
| 2007/0202254 A1* | 8/2007 | Ganguli et al. | 427/252 |
| 2008/0132050 A1* | 6/2008 | Lavoie | 438/584 |
| 2008/0251016 A1 | 10/2008 | Cunning et al. | 118/722 |
| 2008/0282970 A1 | 11/2008 | Heys et al. | 117/104 |
| 2009/0022891 A1 | 1/2009 | Sakai et al. | |
| 2009/0074983 A1 | 3/2009 | Heys et al. | 427/569 |
| 2010/0256406 A1 | 10/2010 | Kanjolia et al. | 556/136 |
| 2010/0261350 A1 | 10/2010 | Kanjolia et al. | 438/681 |
| 2011/0021803 A1 | 1/2011 | Jin et al. | 558/150 |
| 2011/0151227 A1 | 6/2011 | Chalker et al. | 428/220 |
| 2011/0165401 A1 | 7/2011 | Chalker et al. | 428/220 |
| 2011/0165780 A1 | 7/2011 | Kanjolia et al. | 438/785 |
| 2011/0174416 A1 | 7/2011 | Hubsch et al. | 141/1 |
| 2011/0184156 A1 | 7/2011 | Jones | 534/15 |
| 2012/0178266 A1 | 7/2012 | Heys et al. | 438/785 |
| 2013/0041170 A1 | 2/2013 | Odedra et al. | 556/46 |
| 2013/0052368 A1 | 2/2013 | Rushworth et al. | 427/569 |
| 2013/0196065 A1 | 8/2013 | Heys et al. | |

FOREIGN PATENT DOCUMENTS

| | | | |
|---|---|---|---|
| TW | 200540291 | 12/2005 | C23C 16/34 |
| TW | 200746268 | 12/2007 | |
| WO | WO 2006/131751 | 12/2006 | C23C 16/18 |
| WO | WO2007/057631 | 5/2007 | C23C 16/448 |
| WO | WO-2007/121249 A2 | 10/2007 | |
| WO | WO 2009/015270 | 1/2009 | C07F 15/00 |
| WO | WO 2009/015271 | 1/2009 | C07F 15/00 |
| WO | WO 2009/036045 | 3/2009 | C23C 16/455 |
| WO | WO 2009/036046 | 3/2009 | C23C 16/455 |
| WO | WO 2009/086263 | 7/2009 | C23C 16/40 |
| WO | WO 2009/117583 | 9/2009 | C07F 9/09 |
| WO | WO 2009/143452 | 11/2009 | C23C 16/40 |
| WO | WO 2009/143456 | 11/2009 | C23C 6/455 |
| WO | WO 2009/143458 | 11/2009 | C23C 16/40 |
| WO | WO 2009/143460 | 11/2009 | C23C 16/40 |
| WO | WO 2009/146423 | 12/2009 | C23C 16/16 |
| WO | WO 2009/155507 | 12/2009 | C23C 16/18 |
| WO | WO 2009/155520 | 12/2009 | C23C 16/18 |
| WO | WO 2011/011299 | 1/2011 | C23C 16/40 |
| WO | WO 2011/017068 | 2/2011 | C07F 15/06 |
| WO | WO 2011/053505 | 5/2011 | C23C 16/448 |
| WO | WO 2011/097100 | 8/2011 | B01B 1/00 |
| WO | WO 2011/112413 | 9/2011 | C23C 16/00 |
| WO | WO 2011/115878 | 9/2011 | C23C 16/18 |
| WO | WO 2012/027575 | 3/2012 | C07F 11/00 |
| WO | WO-2013112383 A1 | 8/2013 | |

OTHER PUBLICATIONS

Heck, Richard F. Pi-Allylic Ligand Transfer Reactions between Cobalt and Palladium Comlexes, J. Amer. Chem. Soc, 90 (2), Jan. 1968, pp. 317-319.*
Heck, Richard F. Cobalt and Palladium Reagents in Organic Synthesis: The Beginning, Synlett, 1, 2006, pp. 1-6.*
Search Report and Written Opinion dated Apr. 15, 2013 issued in Singapore Application No. 201200801-7.
Dickson, R. S., et al. (1996) "The assessment of some cobalt and cobalt-tellurium complexes for MOCVD applications" Polyhedron, 15(13):2237-2245.
George, S., et al. (1996). "Surface chemistry for atomic layer growth" Journal of Physical Chemistry, 100:13121-13131.
Husebye S., et al. (1964) "Hydrogen shift in the complex formation between deuterium tetracarbonylcobaltate (-I) and 1,4-Pentadiene" Acta Chemica Scandinavica 18(7):1581-1585.
Pankayatselvan R., et al. (1990) "Regioselectivity of nucleophilic additions to substituted ($\eta^4$-diene) Co(CO)$_3$BF$_4$ complexes" Journal of Organometallic Chemistry 384:361-380.
Potter, R., et al. (2005). "Deposition of HfO$_2$, Gd$_2$O$_3$ and PrO$_x$ by liquid Injection ALD techniques" Chemical Vapor Deposition, 11(3):159-169.
International Search Report for PCT/US2010/043300 dated Sep 17, 2010.
Burton, B., et al. (2009) "Atomic layer deposition of MnO using Bis(ethylcyclopentadienyl)manganese and H$_2$O)" Thin Solid Films, 517:5658-5665.
McClellan, W., et al. (1961) "π-Allyl derivatives of transition metals" π-Allyl Derivatives of Transition Metals, 83:1601-1607.
Nilsen, O., et al. (2003) "Growth of manganese oxide thin films by atomic layer deposition" Thin Solid Films, 444:44-51.
Qin, X., et al. (2012) "Thermal chemistry of Mn$_2$(CO)$_{10}$ during deposition of thin manganese films on silicon oxide and on copper surfaces" J. Vac. Sci. Technol. A 30(1):01A112-1-10.
EP Communication for EP Application No. 10738124.6 dated Feb. 11, 2013.
International Preliminary Report on Patentability for International Application No. PCT/US2010/043300 dated Feb. 7, 2012.
Abel, E.W., et al. (1971) "π-Allylcarbonylmetals from σ-Allylorganotin compounds", *Angew. Chem. International Edit.* 10(5).
Palmer, T.G., et al. (1985) "Kinetics and mechanism of substitution reactions of some $\eta^3$-Allyl)manganese Tetracarbonyl compounds", *Journal of American Chemical Society* 107:3122-3129.
Office Action dated Mar. 6, 2014 issued in U.S. Appl. No. 13/569,906.
Japanese Office Action dated Mar. 4, 2014 issued in Japanese Application No. 2012-523641 with English Translation.
Office Action dated Feb. 17, 2014 issued in Chinese Application No. 201080041747.1 with English Translation.

* cited by examiner

HIGH MOLECULAR WEIGHT ALKYL-ALLYL COBALTTRICARBONYL COMPLEXES AND USE THEREOF FOR PREPARING DIELECTRIC THIN FILMS

CROSS-REFERENCE TO RELATED APPLICATIONS

This application is the national phase under 35 U.S.C. §371 of PCT International Application No. PCT/US2010/043300 which has an International filing date of 27 Jul. 2010, which designated the United States of America. This application claims the benefit of U.S. provisional application Ser. No. 61/232,219, filed on 7 Aug. 2009 and U.S. provisional application Ser. No. 61/301,390, filed on 4 Feb. 2010. The disclosure of each recited U.S. provisional application is incorporated by reference in its entirety.

FIELD OF THE INVENTION

The present invention relates to high molecular weight alkyl-allyl cobalttricarbonyl complexes and methods of preparing dielectric thin films by chemical vapor deposition (CVD) or atomic layer deposition (ALD) using such complexes.

BACKGROUND OF THE INVENTION

Various organometallic precursors are used to form high-K dielectric thin metal films. A variety of techniques have been used for the deposition of thin films. These include reactive sputtering, ion-assisted deposition, sol-gel deposition, CVD, and ALD, also known as atomic layer epitaxy. The CVD and ALD processes are being increasingly used as they have the advantages of good compositional control, high film uniformity, good control of doping and, significantly, they give excellent conformal step coverage on highly non-planar microelectronics device geometries.

CVD (also referred to as metalorganic CVD or MOCVD) is a chemical process whereby precursors are used to form a thin film on a substrate. In a typical CVD process, the precursors are passed over a substrate (wafer) within a low pressure or ambient pressure reaction chamber. The precursors react and/or decompose on the substrate surface creating a thin film of deposited material. Volatile by-products are removed by gas flow through the reaction chamber. The deposited film thickness can be difficult to control because it depends on coordination of many parameters such as temperature, pressure, gas flow volumes and uniformity, chemical depletion effects and time.

ALD is a known method for the deposition of thin films. It is a self-limiting, sequential, unique film growth technique based on surface reactions that can provide atomic layer-forming control and deposit-conformal thin films of materials provided by precursors onto substrates of varying compositions. In ALD, the precursors are separated during the reaction. The first precursor is passed over the substrate producing a monolayer on the substrate. Any excess unreacted precursor is pumped out of the reaction chamber. A second precursor is then passed over the substrate and reacts with the first precursor, forming a second monolayer of film over the first-formed monolayer of film on the substrate surface. This cycle is repeated to create a film of desired thickness. ALD film growth is self-limited and based on surface reactions, creating uniform depositions that can be controlled at the nanometer-thickness scale.

Dielectric thin films have a variety of important applications, such as nanotechnology and fabrication of semiconductor devices. Examples of such applications include high-refractive index optical coatings, corrosion-protection coatings, photocatalytic self-cleaning glass coatings, biocompatible coatings, dielectric capacitor layers and gate dielectric insulating films in FETs (Field-Effect Transistor), capacitor electrodes, gate electrodes, adhesive diffusion barriers and integrated circuits. Dielectric thin films are also used in microelectronics applications, such as the high-K dielectric oxide for dynamic random access memory (DRAM) applications and the ferroelectric perovskites used in infrared detectors and non-volatile ferroelectric random access memories (NV-FeRAMs). The continual decrease in the size of microelectronics components has increased the need for the use of such dielectric thin films.

Dickson R., et al. report cobalt complexes for use in MOCVD such as $[(\eta^3-C_3H_5)Co(CO)_3]$, $[(\eta^3-C_3H_4Me)Co(CO)_3]$ and $[(\eta^3-C_3H_5Me_2)Co(CO)_3]$. *Polyhedron*. 15(13): 2237-2245 (1996).

Husebye S, and Jonassen H. report cobalt complexes. *Acta Chem. Scand.* 18(7):1581-1585 (1964).

Pankayatselvan R. and Nicholas, K. report cobalt complexes. *J. Organomet. Chem.* 384:361-380.

Current precursors for use in CVD and ALD do not provide the required performance to implement new processes for fabrication of next generation devices, such as semiconductors. For example, improved thermal stability, higher volatility, reduced vapor pressures, increased deposition rates and a high permittivity are needed.

SUMMARY OF THE INVENTION

In one embodiment, an organometallic precursor corresponding in structure to Formula I is provided:

(Formula I)

wherein $R^1$ is $C_1$-$C_8$-alkyl; $R^2$ is $C_3$-$C_8$-alkyl; x is zero, 1 or 2; and y is 1.

In another embodiment, an organometallic precursor corresponding in structure to Formula I is provided wherein $R^1$ is $C_3$-$C_8$-alkyl; $R^2$ is $C_1$-$C_8$-alkyl; x is 1 or 2; and y is zero or 1.

In another embodiment, a method for forming a cobalt-containing thin film by a vapor deposition process is provided. The method comprises using at least one precursor corresponding in structure to Formula I wherein $R^1$ and $R^2$ are independently $C_2$-$C_8$-alkyl; x is zero, 1 or 2; and y is zero or 1; wherein both x and y can not be zero simultaneously.

Other embodiments, including particular aspects of the embodiments summarized above, will be evident from the detailed description that follows.

DETAILED DESCRIPTION OF THE INVENTION

In various aspects of the invention, substituted-allyl organometallic precursors, methods of making such precursors and methods of using such precursors to form thin metal-containing films, such as but not limited to, metal, metal-oxide or metal-nitride films, are provided.

The methods of the invention are used to create or grow metal-containing thin films which display high dielectric constants. A dielectric thin film as used herein refers to a thin film having a high permittivity.

As used herein, the term "high-κ dielectric" refers to a material, such as a metal-containing film, with a higher dielectric constant (κ) when compared to silicon dioxide (which has a dielectric constant of about 3.7). Typically, a high-κ dielectric film is used in semiconductor manufacturing processes to replace a silicon dioxide gate dielectric. A high-κ dielectric film may be referred to as having a "high-κ gate property" when the dielectric film is used as a gate material and has at least a higher dielectric constant than silicon dioxide.

As used herein, the term "relative permittivity" is synonymous with dielectric constant (κ).

As used herein, the term "precursor" refers to an organometallic molecule, complex and/or compound which is deposited or delivered to a substrate to form a thin film by a vapor deposition process such as CVD or ALD.

As used herein, the term "vapor deposition process" is used to refer to any type of vapor deposition technique such as CVD or ALD. In various embodiments of the invention, CVD may take the form of conventional CVD, liquid injection CVD or photo-assisted CVD. In other embodiments, ALD may take the form of conventional ALD, liquid injection ALD, photo-assisted ALD or plasma-assisted ALD.

The substituted-allyl organometallic precursors of the invention represent substantially improved sources over the previously used unsubstituted precursor, allylCo(CO)$_3$. The unsubstituted precursor, allylCo(CO)$_3$, and even the methyl and dimethyl substituted allylCo(CO)$_3$ precursors are extremely volatile and are not well suited for CVD processes or for controlled thin layer deposition in semiconductor applications. For example, Dickson et al., cited supra, states that "replacing allylic hydrogens by methyl groups does not have a large effect on the magnitude of the vapor pressure." at p. 2242. Surprisingly, in contrast, the inventors have found that the more bulky substituted-allyl precursors actually reduce vapor pressure and thus are easier to handle.

Further, the new precursors have a different volatility which allows for common solvents to be used in their synthesis. This permits a more efficient separation, making it easier to isolate the precursor to very high purity.

The targeted deposition temperatures for these precursors, for example about 90° C. to about 200° C., are lower than for other precursors. Access to low-temperature processing makes integration easier as underlying circuitry does not have to withstand such a high thermal budget.

To date the allyl and methyl-substituted allyl cobalt derivatives yield metal film layers which contain an impermissible level of carbon incorporation. For example greater than about 3% carbon incorporation is considered impermissible. Therefore, in one embodiment, the method forms a cobalt-containing thin film with about 3% or less carbon incorporation. Carbon incorporation should be avoided as it reduces the conductivity of the film and degrades device performance. Without being bound by theory, the inventors propose that the bulky groups substituted on the allyl may decompose via a different mechanism which does not result in as many methyl radicals on the surface. Methyl radicals react to provide very strong metal-carbon bonds, leading to impermissibly high levels of carbon incorporation. The cleaner "leaving" of the organic groups reduces this unwanted reaction and should therefore reduce resistance and improve conductivity of the final films formed.

Further, another advantage of the instant precursors are that they are liquid at room temperature, which is beneficial for handling.

Therefore, in a first embodiment, an alkyl-substituted allyl cobalttricarbonyl organometallic precursor is provided. The organometallic precursor corresponds in structure to Formula I:

(Formula I)

wherein
R$^1$ and R$^2$ are independently C$_2$-C$_8$-alkyl;
x is zero, 1 or 2; and
y is zero or 1;
wherein both x and y can not be zero simultaneously.

It should be noted that the precursors of the invention, represented by the depiction above, have a resonating double bond in the allyl portion and the allyl portion is [C$_3$H$_5$] which is in η$^3$-coordination with the cobalt center. Both of these features are represented by the dashed bonds. When the allyl portion is substituted by one R group, the R group replaces an allylic hydrogen to become [RC$_3$H$_4$], when substituted with two R groups it becomes [R$^1$R$^2$C$_3$H$_3$] where R$^1$ and R$^2$ are the same or different, and so forth.

The term "alkyl" (alone or in combination with another term(s)) refers to a saturated hydrocarbon chain of 1 to about 8 carbon atoms in length, such as, but not limited to, methyl, ethyl, propyl, butyl, pentyl, hexyl, heptyl and octyl. The alkyl group may be straight-chain or branched-chain. "Alkyl" is intended to embrace all structural isomeric forms of an alkyl group. For example, as used herein, propyl encompasses both n-propyl and iso-propyl; butyl encompasses n-butyl, sec-butyl, iso-butyl and tert-butyl. Further, as used herein, "Me" refers to methyl, "Et" refers to ethyl, "iPr" refers to iso-propyl and "tBu" refers to tert-butyl and "Np" refers to neopentyl. It should also be noted that $C_2$ is intended to refer to an ethyl group and not dimethyl.

In one embodiment, $R^1$ and $R^2$ are independently $C_1$-$C_8$-alkyl, particularly $C_2$-$C_8$-alkyl.

In another particular embodiment, $R^1$ and $R^2$ are independently $C_3$-$C_7$-alkyl, and even more particularly $C_4$-$C_7$-alkyl.

In one embodiment, $R^1$ and/or $R^2$ is propyl. Therefore, $R^1$ and/or $R^2$ may be n-propyl, iso-propyl or cyclopropyl.

In another embodiment, $R^1$ and/or $R^2$ is butyl. $R^1$ and/or $R^2$ may be n-butyl, sec-butyl, iso-butyl or tert-butyl. In a particular embodiment, $R^1$ and/or $R^2$ is tert-butyl.

In another embodiment, $R^1$ and/or $R^2$ is pentyl. $R^1$ and/or $R^2$ may be neopentyl ("Np"), straight-chained, or iso-pentyl. In a particular embodiment, $R^1$ and/or $R^2$ is neopentyl.

In another embodiment, $R^1$ and/or $R^2$ is hexyl.

In another embodiment, $R^1$ and/or $R^2$ is heptyl.

In another embodiment, $R^1$ and/or $R^2$ is octyl.

As used herein, the variables, x and y, are used to represent how many particular R substituents are attached to the appropriate carbon.

In one embodiment, the precursor corresponds in structure to Formula I
wherein
$R^1$ is $C_1$-$C_8$-alkyl;
$R^2$ is $C_3$-$C_8$-alkyl;
x is zero, 1 or 2; and
y is 1.

For example, such precursors include but are not limited to:

*note there are not 5 bonds on the terminal carbon here

*note there are not 5 bonds on the terminal carbon here and

In one embodiment, the precursor corresponds in structure to Formula I
wherein
$R^1$ is $C_3$-$C_8$-alkyl;
$R^2$ is $C_1$-$C_8$-alkyl;
x is zero, 1 or 2; and
y is 1.

In one embodiment, if x is zero, 1 or 2, than y is 1. In this embodiment, the organometallic precursor corresponds in structure to Formula Ia:

(Formula Ia)

wherein
$R^1$ and $R^2$ are independently $C_2$-$C_8$-alkyl; and
x is zero, 1 or 2.

In a particular embodiment, x is zero.

In another particular embodiment, x is 1.

In another particular embodiment, x is 2.

In one embodiment, if y is zero, than x is 1 or 2. Thus, in this embodiment, the organometallic precursor corresponds in structure to Formula Ib:

(Formula Ib)

wherein
$R^1$ is $C_2$-$C_8$-alkyl; and
x is 1 or 2.

In a particular embodiment, x is 1.

In another particular embodiment, x is 2.

Examples of such precursors of Formula Ia or Ib include without limitation:

It should be noted that in some embodiments, the center metal can be different from cobalt. For example, the center metal can be Fe, Ru, Ni, Mn, Rh, W, Ta or Ir. These precursors may be used in CVD or ALD methods, such as those mentioned herein, to form their respective metal thin films. For example, these organometallic precursors have the following formula:

wherein M can be any useable metal, for example, Fe, Ru, Ni, Mn, Rh, W, Ta or Ir; and $R^1$, $R^2$, x and y are as defined herein.

In another embodiment, a method to make precursors corresponding in structure to the following formula, $R\text{-allyl}_xM(CO)_{y-x}$, is provided, wherein x=1 or 2 and y=2, 3 or 4; and R is a substituent such as alkyl, alkenyl, alkynyl or alkoxy. The method comprises:

(a) combining $M_2(CO)_{(2y)}$+Na/K in $Me_2O$ at less than −25° C. to yield $M(CO)_y^-$;

(b) combining $M(CO)_y^-$+$R\text{-allyl}_xR^a$ ($R^a$=Cl⁻, Br⁻, F⁻ or other appropriate halide) at less than −25° C. to yield $R\text{-allyl}_xM(CO)_{y-x}$ in solution;

(c) heating $R\text{-allyl}_xM(CO)_{y-x}$ in solution to remove solvent; and (d) distilling off final product, $R\text{-allyl}_xM(CO)_{y-x}$.

In one embodiment, cobalt is used as the metal ("M"). However, the method may be applied to other metals as well, such as Fe, Ru, Ta, Ni, Mn, Rh, W or Ir.

For example $R\text{-allylCo(CO)}_3$ may be prepared. The method comprises:

(a) combining $Co_2(CO)_8$+Na/K in $Me_2O$ at less than −25° C. to yield $Co(CO)_4^-(Na^+/K^+)$ (b) combining $Co(CO)_4^-(Na^+/K^+)$+$R\text{-allyl}R^a$ ($R^a$=Cl⁻, Br⁻, F⁻ or other appropriate halide) at less than −25° C. to yield $R\text{-allylCo(CO)}_3$ in solution;

(c) heating $R\text{-allylCo(CO)}_3$ in solution to remove solvent; and (d) distilling off final product $R\text{-allylCo(CO)}_3$.

The present method is distinguished from the multi-step process used to form the unsubstituted-allyl cobalt precursor, such as $Co_2(CO)_8$+Na/K alloy in THF→$Co(CO)_4^-(Na^+/K^+)$+
removal of THF→Add large amounts of $Et_2O$ at
<0° C.+$R\text{-allyl}R^a$→$R\text{-allylCo(CO)}_3$+$K^+R^a/Na^+$
$R^a$+CO, which can cause a product and solvent separation problem. In contrast, the present method disclosed is a simple, one pot reaction which allows for better control of solvent quantities.

In another embodiment a method of forming a metal-containing film by a vapor deposition process is provided. The method comprises using at least one precursor corresponding in structure to any of the Formulas disclosed herein.

In a particular embodiment, the precursor may be dissolved in an appropriate hydrocarbon or amine solvent. Appropriate hydrocarbon solvents include, but are not limited to, aliphatic hydrocarbons, such as hexane, heptane and nonane; aromatic hydrocarbons, such as toluene and xylene; aliphatic and cyclic ethers, such as diglyme, triglyme and tetraglyme. Examples of appropriate amine solvents include, without limitation, octylamine and N,N-dimethyldodecylamine. For example, the precursor may be dissolved in toluene to yield a 0.05 to 1M solution.

In one embodiment, the vapor deposition process is chemical vapor deposition.

In another embodiment, the vapor deposition process is atomic layer deposition.

The ALD and CVD methods of the invention encompass various types of ALD and CVD processes such as, but not limited to, conventional processes, liquid injection processes, photo-assisted processes and plasma-assisted processes.

In one embodiment, conventional CVD is used to form a metal-containing thin film using at least one precursor according to the Formulas disclosed herein. For conventional CVD processes, see for example Smith, Donald (1995). *Thin-Film Deposition: Principles and Practice*. McGraw-Hill.

In another embodiment, liquid injection CVD is used to form a metal-containing thin film using at least one precursor according to the Formulas disclosed herein.

Examples of liquid injection CVD growth conditions include, but are not limited to:
(1) Substrate temperature: 100-600° C. on Si(100)
(2) Evaporator temperature: 100-200° C.
(3) Reactor pressure: 1-100 mbar
(4) Solvent: toluene, or any solvent mentioned above
(5) Solution concentration: 0.05-0.2 M
(6) Injection rate: 10-50 $cm^3$ $hr^{-1}$
(7) Argon flow rate: 100-300 $cm^3$ $min^{-1}$
(8) Oxygen flow rate: 0-200 $cm^3$ $min^{-1}$
(9) Hydrogen flow rate: 0-200 $cm^3$ $min^{-1}$
(10) Run time: 5-30 min In another embodiment, photo-assisted CVD is used to form a metal-containing thin film using at least one precursor according to the Formulas disclosed herein.

In a further embodiment, conventional ALD is used to form a metal-containing thin film using at least one precursor according to the Formulas disclosed herein. For conventional and/or pulsed injection ALD process see, for example, George S. M., et. al. *J. Phys. Chem.* 1996. 100:13121-13131.

In another embodiment, liquid injection ALD is used to form a metal-containing thin film using at least one precursor according to the Formulas disclosed herein, wherein at least one liquid precursor is delivered to the reaction chamber by direct liquid injection as opposed to vapor draw by a bubbler. For liquid injection ALD process see, for example, Potter R. J., et. al. *Chem. Vap. Deposition.* 2005. 11(3):159.

Examples of liquid injection ALD growth conditions include, but are not limited to:
(1) Substrate temperature: 50-300° C.
(2) Evaporator temperature: 100-200° C.
(3) Reactor pressure: 1-100 5 mbar
(4) Solvent: toluene, or any solvent mentioned above
(5) Solution concentration: 0.05-0.2 M
(6) Injection rate: about 2.50 $pulse^{-1}$ (4 pulses $cycle^{-1}$)
(7) Inert gas flow rate: 100-300 $cm^3$ $min^{-1}$
(8) Reactive gas flow rate: 0-200 $cm^3$ $min^{-1}$
(9) Pulse sequence (sec.) (precursor/purge/reactive gas/ purge): will vary according to chamber size.

(10) Number of cycles: will vary according to desired film thickness.

In another embodiment, photo-assisted ALD is used to form a metal-containing thin film using at least one precursor according to the Formulas disclosed herein. For photo-assisted ALD processes see, for example, U.S. Pat. No. 4,581,249.

In another embodiment, plasma-assisted ALD is used to form a metal-containing thin film using at least one precursor according to the Formulas disclosed herein.

Thus, the organometallic precursors according to the Formulas disclosed herein utilized in these methods may be liquid, solid, or gaseous. Particularly, the precursors are liquid at ambient temperatures with high vapor pressure allowing for consistent transport of the vapor to the process chamber.

In one embodiment, the precursors corresponding to the Formulas disclosed herein are delivered to the substrate in pulses alternating with pulses of an oxygen source, such as a reactive oxygen species. Examples of such oxygen source include, without limitation, $H_2O$, $O_2$ and/or ozone.

In one embodiment a cobalt-containing thin film is formed.

In another embodiment, a cobalt-oxide thin film is formed.

In another embodiment, a cobalt-nitride thin film is formed.

In another embodiment, two or more precursors corresponding in structure to the Formulas disclosed herein may be used to form a thin film.

In another embodiment a "mixed" metal thin film is formed. This method comprises using at least one "co-precursor" to form a "mixed" metal film. As used herein, a mixed-metal film contains at least two different metals.

In a particular embodiment, a cobalt precursor corresponding in structure to the Formulas disclosed herein may be used in CVD or ALD with at least one Ta, Si, Fe, Ru, Ni, Mn, Rh, W, Ir precursor to form a mixed-metal film, such as a cobalt-tantalum film, a cobalt-silicon film, a cobalt-iron film, etc.

In one embodiment, a thin film comprising cobalt and silicon is formed.

In a particular embodiment a mixed-metal oxide thin film is formed, such as a cobalt-silicon oxide thin film.

In a particular embodiment a mixed-metal nitride thin film is formed, such as a cobalt-silicon nitride thin film.

A dielectric film can also be formed by the at least one precursor corresponding to the Formulas disclosed herein, independently or in combination with a co-reactant. Examples of such co-reactants include, but are not limited to, hydrogen, hydrogen plasma, oxygen, air, water, $H_2O_2$, ammonia, hydrazine, alkyl-substituted hydrazine, borane, silane, ozone or any combination thereof.

In a particular embodiment, a co-reactant such as hydrazine or an alkyl-substituted hydrazine is used to form a film using at least one precursor corresponding to the Formulas disclosed herein. For example, N,N-dimethylhydrazine (DMHz), tert-butylhydrazine and/or trisilane may be used as a co-reactant.

A variety of substrates can be used in the methods of the present invention to support thin films. For example, the precursors according to the Formulas disclosed herein may be delivered for deposition to substrates such as, but not limited to, silicon, silicon oxide, silicon nitride, tantalum, tantalum nitride, copper, ruthenium, titanium nitride, tungsten, and tungsten nitride.

In one embodiment, the method is used for applications such as dynamic random access memory (DRAM) and complementary metal oxide semi-conductor (CMOS) for memory and logic applications on, for example, silicon chips.

Fundamental differences exist between the thermally-driven CVD process and the reactivity-driven ALD process. The requirements for precursor properties to achieve optimum performance vary greatly. In CVD a clean thermal decomposition of the precursor to deposit the required species onto the substrate is critical. However, in ALD such a thermal decomposition is to be avoided at all costs. In ALD the reaction between the input reagents must be rapid and result in the target material formation on the substrate. However, in CVD any such reaction between species is detrimental due to their gas phase mixing before reaching the substrate to generate particles. In general it is accepted that a good CVD source will be a poorer ALD source and vice versa and therefore it is surprising that the substituted-allyl precursors of this invention perform well in both ALD and CVD processes albeit under different process conditions.

The substituted-allyl precursors offer access to different temperature windows for deposition processes when compared to conventional precursors. This makes matching of these substituted-allyl precursors with other metal sources open to more manipulation when attempting to deposit ternary or quaternary alloys in an optimized fashion.

EXAMPLES

The following examples are merely illustrative, and do not limit this disclosure in any way.

Conventional synthesis processes use $Et_2O$ as solvent. Raw materials/intermediates are not very soluble in $Et_2O$ and thus need large amounts of solvent. Alternative solvents in which these materials are more soluble, for example THF (tetrahydrofuran)-$Me_2O$, are better for scale up and reduction in chemical volumes needed.

For the unsubstituted precursor, allylCo$(CO)_3$, THF cannot be used as solvent because it has a similar volatility to the product and so cannot be separated. Two steps allow efficient use of THF in the first reduction step and then it is replaced by a more volatile solvent $Me_2O$ rather than $Et_2O$ to minimize solvent requirements during the product formation step while still allowing facile isolation of pure compounds due to easy solvent removal. The novel compounds of this invention widen the gap between volatilities enabling THF and the products to be separated. Therefore a single solvent can be used for all steps allowing a novel one pot processes proposed.

Example 1

Two Step Process to Prepare Co($\eta^3$-tert-butylallyl)(CO)$_3$ or Co($\eta^3$-neopentylallyl)(CO)$_3$ Step 1

A solution of $CO_2(CO)_8$ (44.6 g, 0.142 mols) in THF (ca 600 ml) was added drop-wise over two hours to a suspension of NaK (16 ml of 22/78) in THF (ca 150 ml) cooled to 0° C.

The solution was stirred for ca 1 hour, filtered through a small plug of celite and the solvent removed in vacuo. The very pale yellow solid isolated was subsequently dried overnight at 50° C. to remove all traces of THF.

Step 2

Co($\eta^3$-tert-butylallyl)(CO)$_3$

K[Co(CO)$_4$] (26.2 g, 0.125 mol) from step 1 was dissolved in Me$_2$O (ca 175 ml) in a flask cooled with dry ice and fitted with a −50° C. condenser. Tert-butylallyl bromide (2-bromomethyl-3,3-dimethylbut-1-ene, 22.1 g, 18.4 ml, 0.125 mols) was added to the reaction mixture. The dry-ice cooling was removed and the reaction mixture allowed to warm with stifling overnight. The now dark-red/brown mixture had a precipitate just visible. The Me$_2$O was allowed to boil off over several hours and the oily residue extracted with pentane (2×50 ml), filtered through a small plug of celite and the celite washed with pentane (2×20 ml).

Most of the pentane was removed on a water pump vacuum and the thick liquid transferred into a 250 ml flask. Distillation up a 10 cm B14 Vigreux column gave 19.2 g (64%) of a yellow/brown fraction starting at 79° C., and a second, major fraction at 85-87° C.@17 mmHg.

IR (hexane): 2063m, 2000s, 1994s sm$^{-1}$

NMR (C$_6$D$_6$) $^1$H; 0.87 (s, 9H, $^t$Bu), 1.65 (s, 2H, H$_{anti}$), 2.74 (s, 2H, H$_{syn}$), $^{13}$C{$^1$H} 30.3 (s, $^t$Bu), 34.0 (s, C$^t$Bu), 46.8 (s, CH$_2$), 113.8 (s, C), 204.0 (s, br, CO)

Analysis Calc: % C=50.0, % H=5.5, % Co=24.5

Co($\eta^3$-neopentylallyl)(CO)$_3$

K[Co(CO)$_4$] (22.8 g, 0.109 mol) from step 1 was dissolved in Me$_2$O (ca 100 ml in a flask cooled with dry ice and fitted with a −50° C. condenser. Neopentylallyl bromide (2-bromomethyl-4,4-dimethylpent-1-ene (23.5 g, 0.123 mols) was added drop-wise to the reaction mixture which was cooled to −78° C. The dry-ice cooling was removed and the reaction mixture allowed to warm with stirring overnight. The now dark-red/orange mixture had a precipitate just visible. The Me$_2$O was allowed to boil off over several hours and the product was extracted with pentane (4×50 ml), filtered through a small plug of celite and the bulk of the pentane removed on a water pump (13 mmHg). The material was distilled using an oil bath at 3-4 mm Hg. A pale yellow liquid began to distil at 50° C. (about 3 ml, 4.1 g) then the temperature rose to 72° C. This material was collected separately as a dark orange-red liquid (16.4 g, 59%).

IR (hexane) 2062m, 1996s cm$^{-1}$

NMR (C$_6$D$_6$) $^1$H; 0.76 (s, 9H, $^t$Bu), 1.70 (s, 2H, CH$_2$), 1.87 (s, 2H, H$_{anti}$), 2.77 (s, 2H, H$_{syn}$), $^{13}$C{$^1$H} 29.3 (s, $^t$Bu), 32.1 (s, C$^t$Bu), 54.1 (s, CH$_2$Bu$^t$), 54.2 (s CH$_2$), 101.4 (s, C), 203.8 (s, br, CO) Analysis Calc: % C=51.98, % H=5.95, % Co=23.19

Example 2

Single Step Process to Prepare Co($\eta^3$-tert-butylallyl)(CO)$_3$ or Co($\eta^3$-neopentylallyl)(CO)$_3$ Co($\eta^3$-tert-butylallyl)(CO)$_3$ Using THF as Solvent A solution of CO$_2$(CO)$_8$ (22.3 g, 0.071 mols) in THF (ca 600 ml) is added drop-wise over two hours to a suspension of NaK (8 ml of 22/78) in THF (ca 150 ml) cooled to 0° C. and then stirred for ca 1 hour. Tert-butylallyl bromide (2-bromomethyl-3,3-dimethylbut-1-ene, 22.1 g, 18.4 ml, 0.125 mols) is added to the reaction mixture at −30° C. and the reaction mixture stirred overnight at this temperature. The reaction mixture is allowed to warm prior to THF removal under vacuum and residue extraction with pentane (4×50 ml). After filtering the pentane is removed under vacuum and the product collected by distillation at 85-87° C.@ 17 mmHg.

Co($\eta^3$-tert-butylallyl)(CO)$_3$ Using Me$_2$O as Solvent

A solution of CO$_2$(CO)$_8$ (22.3 g, 0.071 mols) in Me$_2$O (ca 600 ml) is added drop-wise over two hours to a suspension of NaK (8 ml of 22/78) in Me$_2$O (ca 150 ml) cooled to −30° C. and then stirred for ca 2 hours. Tert-butylallyl bromide (2-bromomethyl-3,3-dimethylbut-1-ene, 22.1 g, 18.4 ml, 0.125 mols) is added to the reaction mixture at −30° C. and the whole is stirred overnight at this temperature. The cooling is then removed and the Me$_2$O is allowed to boil off and the residue extracted with pentane (4×50 ml). After filtering the pentane is removed under vacuum and the product collected by distillation at 85-87° C.@17 mmHg.

Co($\eta^3$-neopentylallyl)(CO)$_3$ Using THF as Solvent

A solution of CO$_2$(CO)$_8$ (22.3 g, 0.071 mols) in THF (ca 600 ml) is added drop-wise over two hours to a suspension of NaK (8 ml of 22/78) in THF (ca 150 ml) cooled to 0° C. and then stirred for ca 1 hour. Neopentylallyl bromide (2-bromomethyl-4,4-dimethylpent-1-ene (23.9 g, 0.125 mols is added to the reaction mixture at −30° C. and the reaction mixture stirred overnight at this temperature. The reaction mixture is allowed to warm prior to THF removal under vacuum and residue extraction with pentane (4×50 ml). After filtering the pentane is removed under vacuum and the product collected by distillation at 72° C.@3-4 mmHg Co($\eta^3$-neopentylallyl)(CO)$_3$ using Me$_2$O as solvent A solution of CO$_2$(CO)$_8$ (22.3 g, 0.071 mols) in Me$_2$O (ca 600 ml) is added drop-wise over two hours to a suspension of NaK (8 ml of 22/78) in Me$_2$O (ca 150 ml) cooled to −30° C. and then stirred for ca 2 hours. Neopentylallyl bromide (2-bromomethyl-4,4-dimethylpent-1-ene (23.9 g, 0.125 mols) is added to the reaction mixture at −30° C. and the whole is stirred overnight at this temperature. The cooling is then removed and the Me$_2$O is allowed to boil off and the residue extracted with pentane (4×50 ml). After filtering the pentane is removed under vacuum and the product collected by distillation at 72° C.@3-4 mmHg

Figure 1:
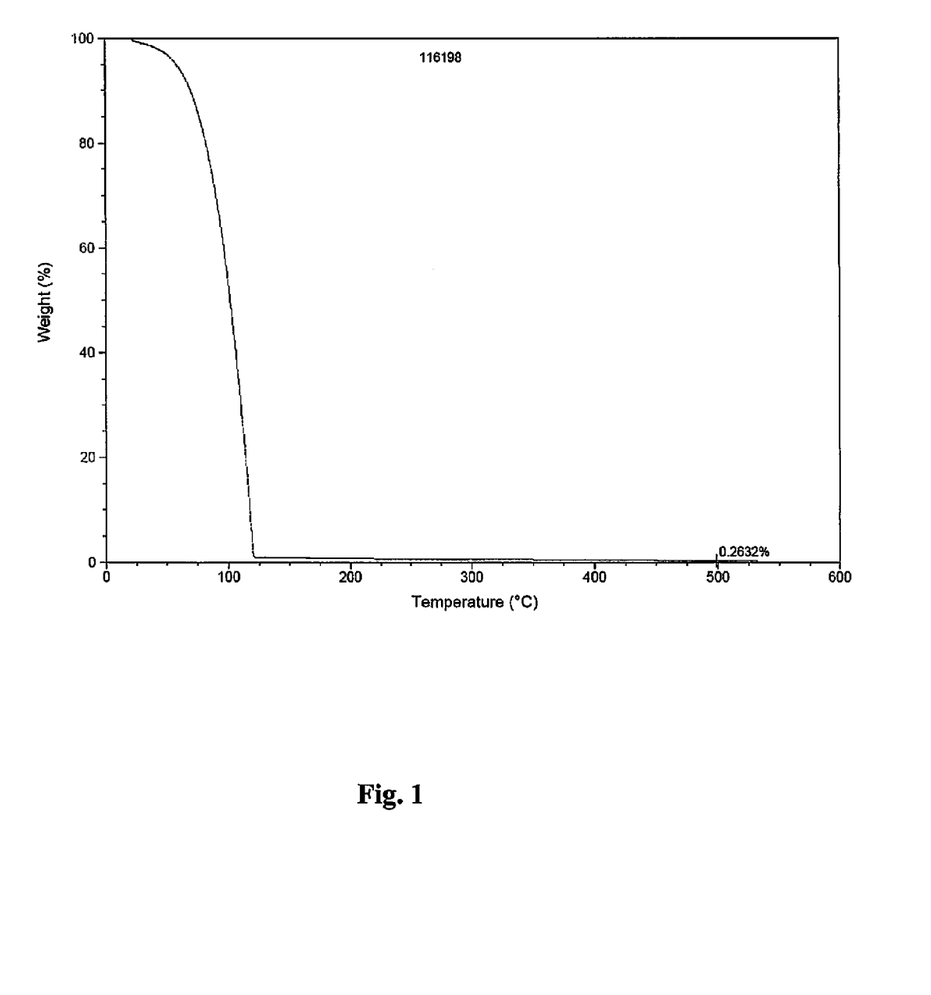
FIG. 1 is a graphical representation of TGA (thermal gravimetric analysis) data demonstrating % weight loss vs. temperature of (t-butyl)allylCo(CO)$_3$.

FIG. 1 represents TGA data for (t-butyl)allylCo(CO)$_3$.

Figure 2:
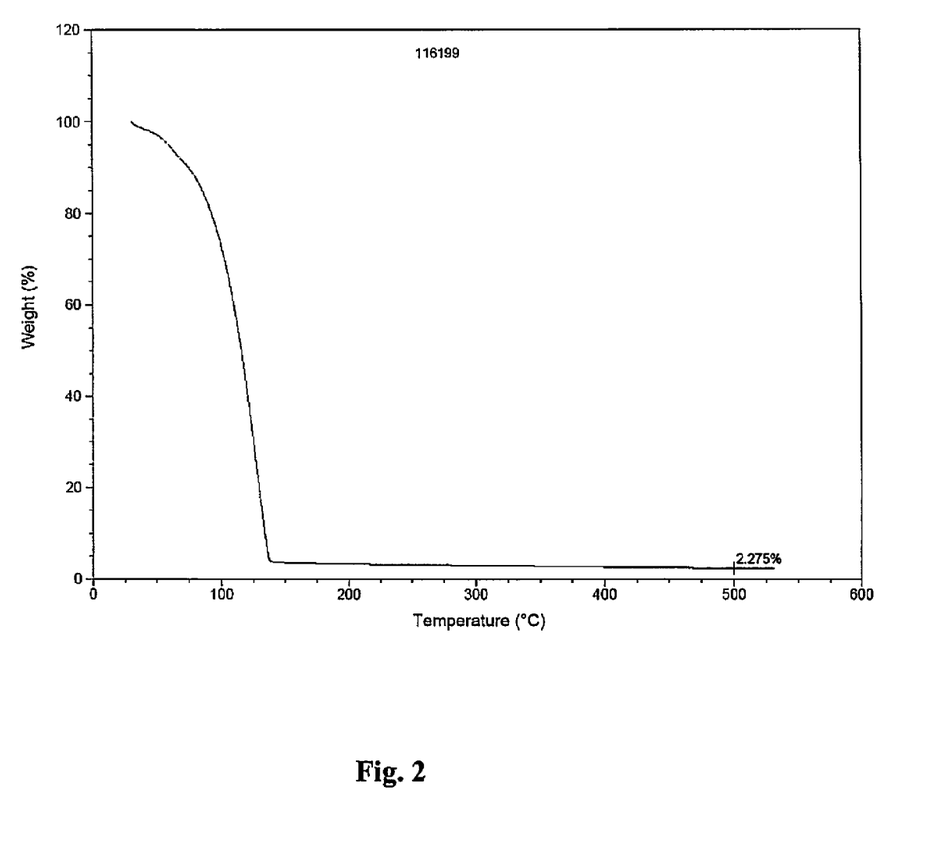
FIG. 2 is a graphical representation of TGA data demonstrating % weight loss vs. temperature of (neopentyl)allylCo(CO)$_3$.

FIG. 2 represents TGA data for (Np)allylCo(CO)$_3$

Example 3

CVD Study

Conventional, pulsed CVD experiments were carried out using a home-made tool fitted with bubbling/vapor draw precursor inlet system. During the CVD experiments targeting pure metal, nitrogen gas was employed as carrier/purge gas. Films were deposited on H-terminated silicon or thermal silicon oxide using neat samples of either (1) (t-butyl)allylCo(CO)$_3$ or (2) (Np)allylCo(CO)$_3$, each depicted below:

For CVD using (Np)allylCo(CO)$_3$ as a precursor source (45° C.), a vapor draw precursor delivery method was used. Runs were done with a substrate temperature of 150° C. and 500 cycles with N,N-dimethylhydrazine as co-reagent/reactant.

| CVD Growth Conditions using (Np)allylCo(CO)$_3$ | |
|---|---|
| Ampoule temperature | 45° C. |
| Substrate Temperature(s) | 150° C. |
| Carrier gas | 0 sccm N$_2$ |
| Temperature of Lines to chamber | 60° C. |
| Purge gas | 10 sccm N$_2$ |
| Base pressure during run | 100 mtorr |
| Pulse sequence | 0.5 s pulse every 20 s |

Figure 3:
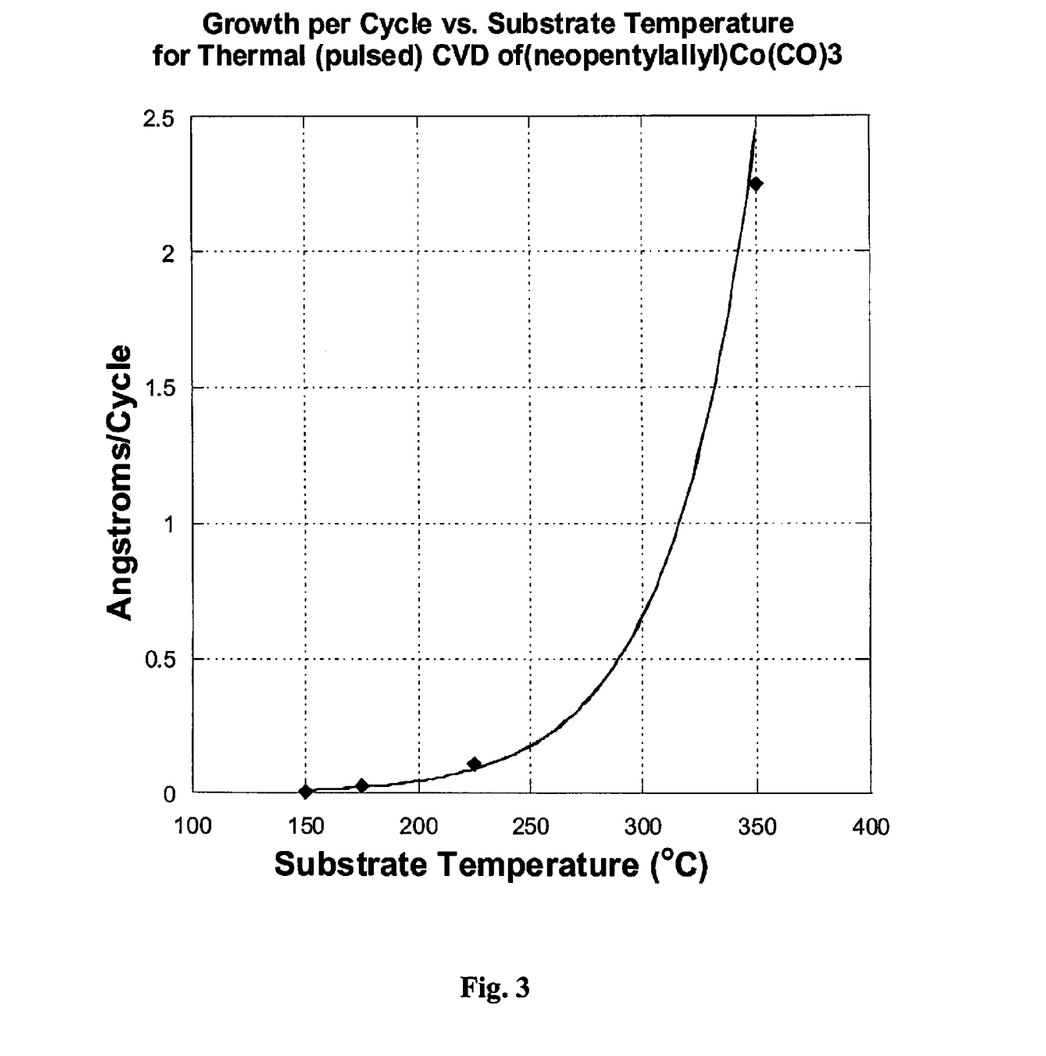
FIG. 3 is a graphical representation of pulsed CVD growth per cycle (Angstroms/cycle) vs. temperature using (neopentyl)allylCo(CO)$_3$.

FIG. 3 displays thermal decomposition of (Np)allylCo(CO)$_3$ with respect to temperature (growth per cycle (Angstroms/Cycle)) vs. substrate temperature).

For CVD using (t-butyl)allylCo(CO)$_3$ as a precursor source (35° C.), bubbling delivery method was used. Runs were done with a substrate temperature of 150° C. and 500 cycles with N,N-dimethylhydrazine as co-reagent/reactant.

| CVD Growth Conditions using (t-butyl)allylCo(CO)$_3$ | |
|---|---|
| Ampoule temperature | 35° C. |
| Substrate Temperature(s) | 150° C. |
| Carrier gas | 0 sccm N$_2$ |
| Temperature of Lines to chamber | 45° C. |
| Purge gas | 10 sccm N$_2$ |
| Base pressure during run | 100 mtorr |
| Pulse sequence | 0.5 s pulse every 20 s |

Figure 4:
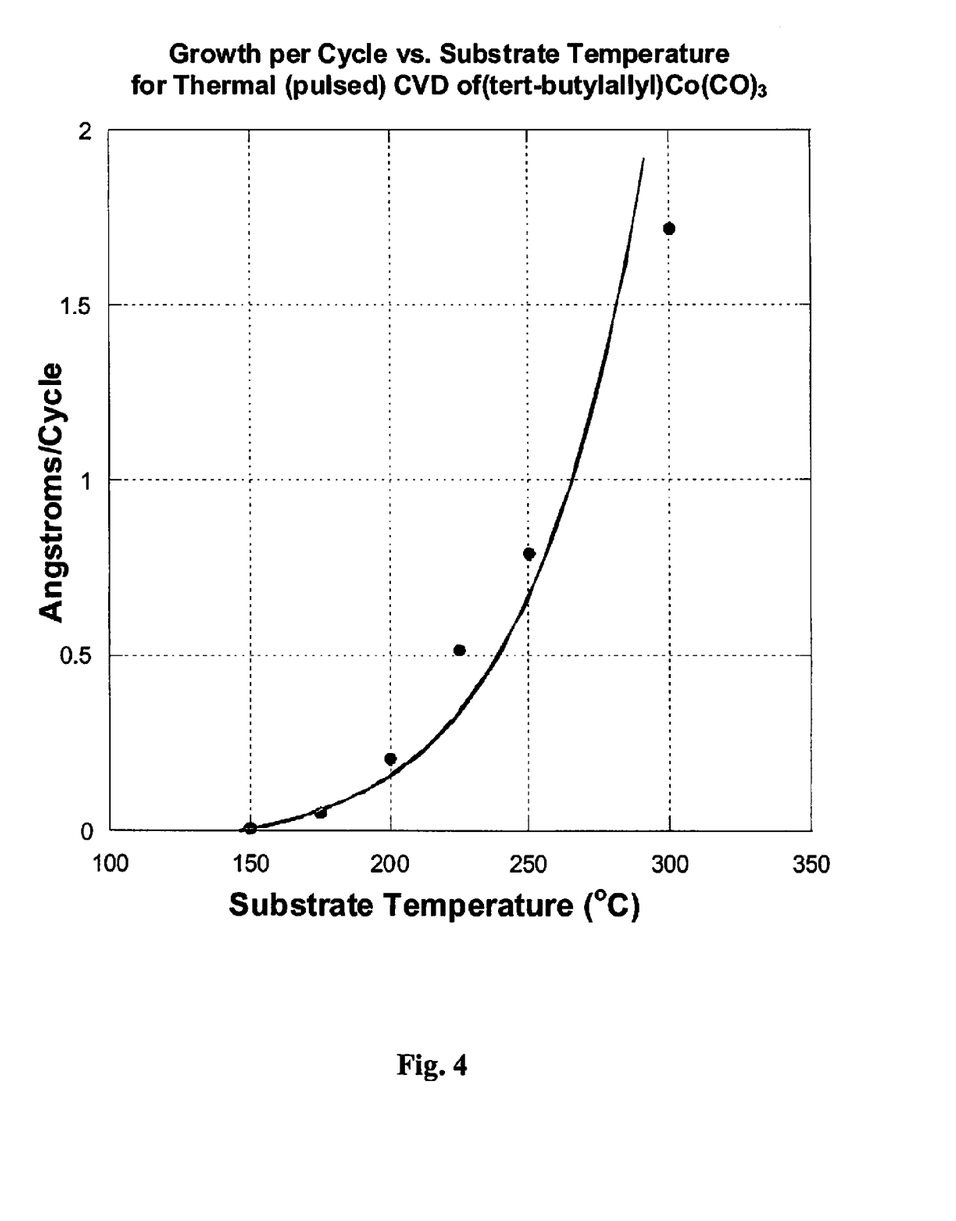
FIG. 4 is a graphical representation of pulsed CVD growth per cycle (Angstroms/cycle) vs. temperature using (t-butyl)allylCo(CO)$_3$.

FIG. 4 displays thermal decomposition of (t-butyl)allylCo(CO)$_3$ with respect to temperature (growth per cycle (Angstroms/Cycle)) vs. substrate temperature).

Example 4

ALD Study

Conventional ALD experiments were carried out using a home-made tool fitted with bubbling/vapor draw precursor inlet system. A vapor draw precursor delivery method was used for each precursor. The ALD experiments targeted pure metal, and nitrogen gas was employed as carrier/purge gas and was employed in the alternating pulse cycle. Each precursor was used at 50° C. Runs were done with a substrate temperature of 150° C. with N,N-dimethylhydrazine as co-reagent/reactant. Films were deposited on H-terminated silicon or thermal silicon oxide using neat samples of either (1) (t-butyl)allylCo(CO)$_3$ or (2) (Np)allylCo(CO)$_3$, each depicted below:

Growth conditions were the same for each precursor.

| ALD Growth Conditions | |
|---|---|
| Substrate temperature | 150° C. |
| Number of cycles | 300-1000 |
| Pulse sequence (sec.) | 0.2 sec/10 sec N$_2$ purge/0.2 |
| [Co precursor]/purge/[coreagent]/purge/-- | sec DMHz/10 sec N$_2$ purge |

Figure 5:
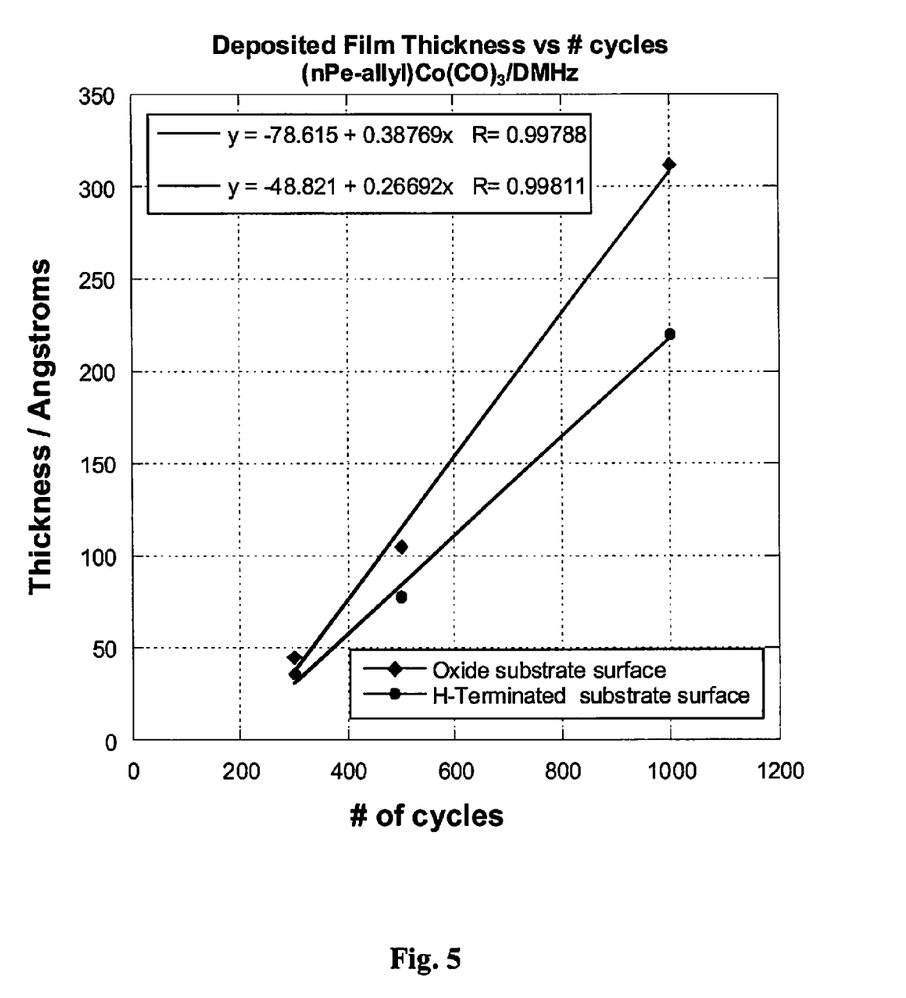
FIG. 5 is a graphical representation of thickness (Angstroms) vs. number of cycles using (neopentyl)allylCo(CO)$_3$ and Me$_2$NNH$_2$ in ALD growth with a substrate temperature of 150° C.

FIG. 5 is a graphical representation of thickness (Angstroms) vs. number of cycles using (Np)allylCo(CO)$_3$.

Figure 6:
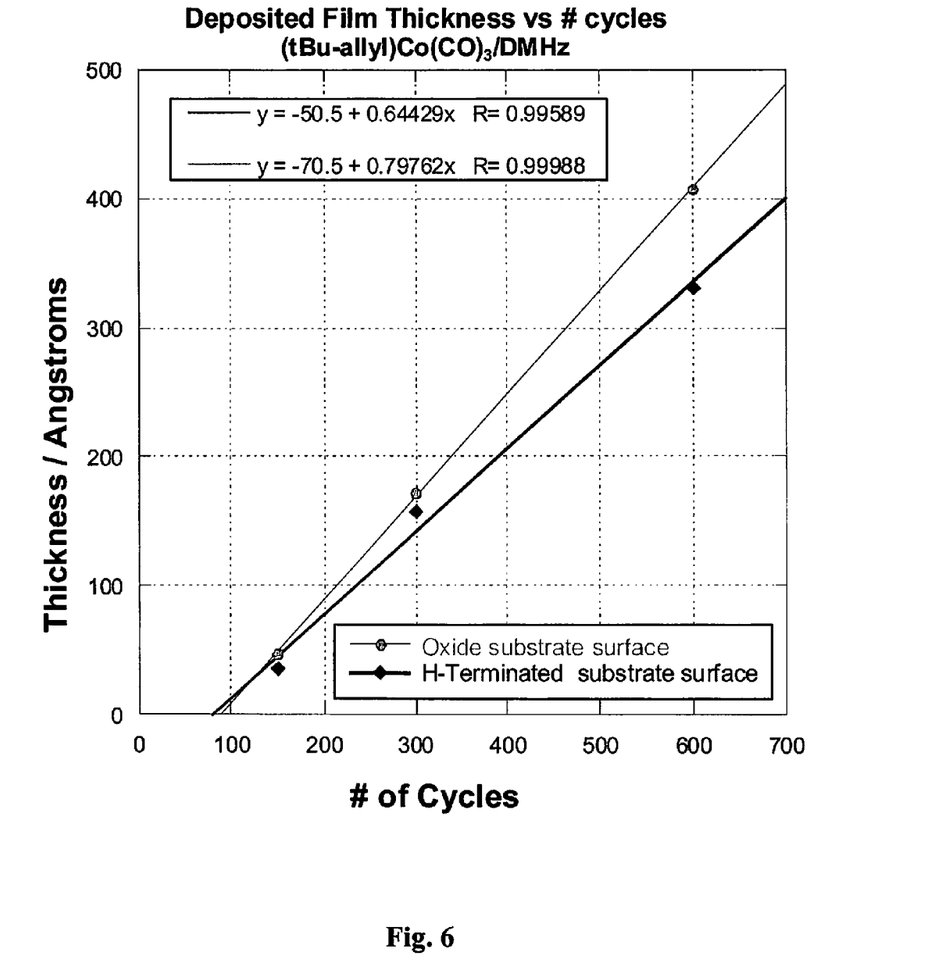
FIG. 6 is a graphical representation of thickness (Angstroms) vs. number of cycles using (t-butyl)allylCo(CO)$_3$ and Me$_2$NNH$_2$ in ALD growth with a substrate temperature of 150° C.

FIG. 6 is a graphical representation of thickness (Angstroms) vs. number of cycles using (t-butyl)allylCo(CO)$_3$.

It is now discovered that the new precursors, (Np)allylCo(CO)$_3$ and (t-butyl)allylCo(CO)$_3$, have a higher thermal stability than the unsubstituted, (allyl)Co(CO)$_3$, which allows for ALD processes that are not attainable with (allyl)Co(CO)$_3$ due to its low thermal decomposition temperature.

(Np)allylCo(CO)$_3$ and (t-butyl)allylCo(CO)$_3$ are thermally stable up to 150° C. with no CVD observed at this temperature. Unlike the unsubstituted precursor, (allyl)Co(CO)$_3$, (Np)allylCo(CO)$_3$ and (t-butyl)allylCo(CO)$_3$ have shown ALD behavior at a temperature below the CVD window. When used in combination with hydrazines, such as N,N-dimethylhydrazine or t-butylhydrazine, ALD growth of cobalt film is observed at substrate temperatures of 150° C. Therefore, bulky-substituted allyl precursors, such as (Np)allylCo(CO)$_3$ and (t-butyl)allylCo(CO)$_3$, are clearly much better suited to deposition of high quality films using ALD. The ability to perform ALD below the CVD window with (Np)allylCo(CO)$_3$ and (t-butyl)allylCo(CO)$_3$, but not with the unsubstituted or small-alkyl substituted precursors, is surprising.

All patents and publications cited herein are incorporated by reference into this application in their entirety.

The words "comprise", "comprises", and "comprising" are to be interpreted inclusively rather than exclusively.

What is claimed is:

1. A method for forming a cobalt-containing thin film by a vapor deposition process, the method comprising using at least one precursor corresponding in structure to Formula I:

(Formula I)

wherein
R$^1$ and R$^2$ are independently C$_4$-C$_8$-alkyl;
x is zero, 1 or 2; and
y is zero or 1;
wherein both x and y cannot be zero simultaneously.

2. The method of claim 1, wherein y is 1 and x is zero, 1 or 2.

3. The method of claim 1, wherein y is zero and x is 1 or 2.

4. The method of claim 1, wherein y is 1 and x is 1.

5. The method of claim 1, wherein y is 1 and x is 2.

6. The method of claim 1, wherein the at least one precursor is selected from the group consisting of:

7. The method of claim 1, wherein the vapor deposition process is chemical vapor deposition.

8. The method of claim 7, wherein the chemical vapor deposition is liquid injection chemical vapor deposition.

9. The method of claim 1, wherein the vapor deposition process is atomic layer deposition.

10. The method of claim 9, wherein the atomic layer deposition is liquid injection atomic layer deposition or pulsed injection atomic layer deposition.

11. The method of claim 1, wherein the at least one precursor is delivered to a substrate in pulses alternating with pulses of an oxygen source selected from the group consisting of $H_2O$, $O_2$ and ozone to form a metal oxide film.

12. The method of claim 11, further comprising using at least one co-precursor having a metal selected from the group consisting of Ta, Si, Fe, Ru, Ni, Mn, Rh, W and Ir to form a mixed-metal oxide film.

13. The method of claim 12, wherein the mixed-metal oxide film comprises cobalt and silicon.

14. The method of claim 1, further comprising using at least one appropriate co-reactant selected from the group consisting of hydrogen, hydrogen plasma, oxygen, air, water, ammonia, a hydrazine, an alkyl-substituted hydrazine, a borane, a silane, ozone and a combination thereof.

15. The method of claim 11, further comprising using an alkyl-substituted hydrazine as a co-reactant to form a cobalt-containing thin film.

16. The method of claim 1, wherein the thin film formed comprises a cobalt-nitride thin film.

17. An organometallic precursor corresponding in structure to Formula I:

(Formula I)

wherein
$R^1$ is $C_1$-$C_8$-alkyl;
$R^2$ is $C_4$-$C_8$-alkyl;
x is zero, 1 or 2; and
y is 1.

18. The precursor of claim 17, wherein the precursor is

19. An organometallic precursor corresponding in structure to Formula I:

(Formula I)

wherein
$R^1$ is $C_4$-$C_8$-alkyl;
$R^2$ is $C_1$-$C_8$-alkyl;
x is 1 or 2; and
y is zero or 1.

20. The precursor of claim 19, wherein the precursor is

* * * * *